United States Patent [19]

Crews, Jr.

[11] Patent Number: 4,718,281

[45] Date of Patent: Jan. 12, 1988

[54] BEARING-BYPASS MATERIAL SYSTEM TEST

[75] Inventor: John H. Crews, Jr., Grafton, Va.

[73] Assignee: The United States of America as represented by the Administrator, National Aeronautics & Space Administration, Washington, D.C.

[21] Appl. No.: 13,802

[22] Filed: Feb. 12, 1987

[51] Int. Cl.⁴ .............................................. G01N 3/36
[52] U.S. Cl. ..................................... 73/794; 73/810
[58] Field of Search .................. 73/794, 796, 798, 808, 73/810, 813

[56] References Cited

U.S. PATENT DOCUMENTS

| | | |
|---|---|---|
| 3,546,931 | 12/1970 | Crews, Jr. et al. . |
| 3,590,633 | 7/1971 | Fuhrmann et al. . |
| 3,664,179 | 5/1972 | Danko et al. ...................... 73/798 X |
| 3,757,568 | 9/1973 | Fletcher et al. . |
| 3,844,167 | 10/1974 | Schutzler . |

OTHER PUBLICATIONS

"Bolted Joint Design", R. L. Ramkumar, A symposium sponsored by ASTM Committee D-30 on High Modulus Fibers and Their Composites, *American Society for Testing and Materials,* Dearborn, Mich., 2-3 Oct. 1979, pp. 376-395.

"Effects of Bearing/Bypass Load Interaction on Laminate Strength", S. P. Garbo, AFWAL-TR-81-3114, Sep. 1-81, pp. 1-25.

"Design Verification Testing of the X-29 Graphite/Epoxy Wing Covers, G. Concannon, 1983 Fall Meeting Proceedings, Society for *Experimental Stress Analysis,* Nov. 6-10, 1983, pp. 96-102.

*Primary Examiner*—Jerry W. Myracle
*Attorney, Agent, or Firm*—George F. Helfrich; John R. Manning

[57] ABSTRACT

A material specimen 12 containing a central hole is bolted (bolt 27) between two bearing guide plates 28 and 29. An applied load control 11 applies an applied load, either tension or compression, to one end of specimen 12 and a bypass load control 13 applies a bypass load to the other end of specimen 12. Both load controls have their control inputs supplied by a single input signal generator 24. The difference between the applied load and the bypass load is transmitted through bolt 27 and plates 28 and 29 to bearing load cells 30 and 31.

10 Claims, 1 Drawing Figure

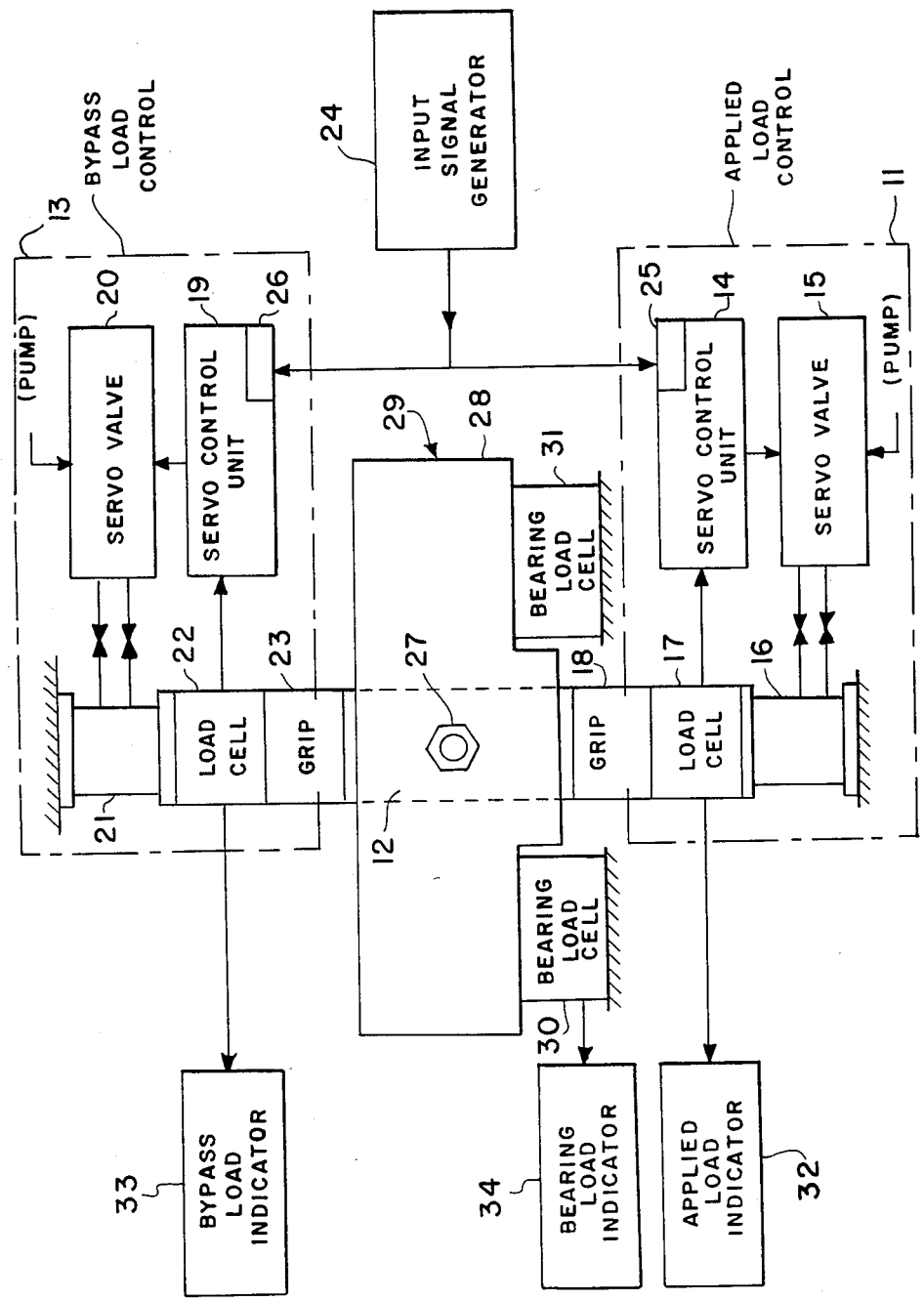

BEARING-BYPASS MATERIAL SYSTEM TEST

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

The invention relates generally to material testing and more specifically concerns bearing-bypass testing of mechanically-fastened joints in materials such as composites.

In the past, design procedures for mechanically-fastened joints in composites have usually been very conservative. In such cases, failures were usually avoided by heavily reinforcing the laminates in the vicinity of the joints. Needed improvements in joint efficiency require data bases for laminates tested under conditions typical of structural joints. Within a multi-fastener structural joint, fastener holes may be subjected to the combined effects of bearing loads and loads that bypass the hole. The ratio of bearing load to bypass load depends on the joint stiffness and configuration. As the joint is loaded, this bearing-bypass ratio remains nearly constant until damage develops. Although the combined effects of bearing and bypass loads can be simulated by testing single-fastener specimens, such tests are difficult.

Three approaches to bearing-bypass testing have been used in the past with simple specimens. The first approach uses levers and linkages to divide the applied load into two proportional parts. One part acts on the end of the specimen and the other is reacted as a bearing load at the specimen hole. The bolt hole is thereby subjected to proportional bearing and bypass loading. The lever fulcrum points can be changed to produce different ratios of bearing to bypass loading. This lever-linkage approach works well for tension bearing-bypass loading, but is difficult to apply in compression.

The second approach to bearing-bypass testing uses a "scissor" mechanism to apply a bearing load between two holes in the test specimen. This bearing load is held constant while the bypass load is increased until the specimen fails. Although this approach does produce bearing-bypass loading in tension or compression, it does not maintain the desired constant ratio of bearing to bypass loads. Furthermore, this approach could alter the sequence of local damage development.

The third approach used two control systems: one controls the bearing load while the other controls the bypass load. The bypass load is applied to one end of the specimen in the conventional manner; however, the bearing load is applied through linkages with two hydraulic cylinders connected to the ends of a bearing bar which is bolted to the specimen. Although this concept works in tension and compression the test apparatus is rather complex and quite different apparatus arrangements are needed by the two types of loading.

An object of this invention is to provide bearing-bypass testing approach with a constant bearing-bypass load ratio throughout.

Another object of this invention is to provide a simple approach for combined bearing-bypass testing that works equally well in tension and compression.

Another object of this invention is to provide bearing-bypass testing that requires no change in apparatus in tension and compression testing.

Other objects and advantages of this invention will become apparent hereinafter in the specification and drawing.

BRIEF DESCRIPTION OF THE INVENTION

The invention consists essentially of an applied load control for applying applied loads (either tension or compression) to one end of a specimen and a bypass load control for applying bypass loads to the other end of the specimen. Two bearing guide plates are bolted to the specimen through a central hole in the specimen and attached to bearing load cell means. Consequently, the difference between the applied load and the bypass load is transmitted through the specimen, the bolt, and the bearing guide plates to the bearing load cell means which measures the difference. This measurement is the bearing load.

In operation an input signal generator applies its output to both the applied load control and the bypass load control. The applied and bypass controls are adjusted to provide a desired ratio between the applied and bypass loads. Then the output of the signal generator is increased until the specimen fails.

BRIEF DESCRIPTION OF THE DRAWING

The sole FIGURE in this application is a schematic of the invention.

DETAILED DESCRIPTION OF THE INVENTION

Turning now to the embodiment of the invention selected for illustration in the drawing, the number 11 indicates an applied load control for applying an applied load to one end of a test specimen 12. A bypass load control 13 is for applying a bypass load to the other end of specimen 12. Applied load control 11 includes a servo control unit 14, a servo valve 15 for controlling the flow of a fluid from a pump (not shown) into and out of a hydraulic cylinder 16, a load cell 17 attached to hydraulic cylinder 16, and a grip 18 attached to hydraulic cylinder 17 for gripping one end of specimen 12. Bypass load control 13 includes a servo control unit 19, a servo valve 20 for controlling the flow of a fluid from a pump (not shown) into and out of a hydraulic cylinder 21, a load cell attached to hydraulic cylinder 21, and a grip 23 attached to load cell 22 for gripping the other end of specimen 12. These load control units are conventional servo units having their inputs connected to an input signal generator 24. The output of the signal generator is applied to servo control units 14 and 19 through voltage controls 25 and 26, respectively. These voltage controls are for selecting desired portions of the output from signal generator 24. Voltage controls are usually supplied with the servo units, but if not, the voltage controls can be a potentiometer or a variable resistor as is well known in the art. The reason that a single generator 24 is used instead of two separate generators is that the voltages applied to the servo units should be exactly the same except for amplitude.

Specimen 12 has a central hole in it and is bolted, by means of a bolt 27 through the central hole, to two identical bearing guide plates 28 and 29 (not shown). Specimen 12 is "sandwiched" between plates 28 and 29. Two bearing load cells 30 and 31 are attached to bearing guide plates 28 and 29 equidistance from the center of specimen 12 and are fixed relative to the fixed end of hydraulic cylinder 16. Consequently, the combined outputs from bearing load cells 30 and 31 will measure the total bearing load on bolt 27. An applied load indicator 32, a bypass load indicator 33, and a bearing load indicator 34 indicate the loads applied to load cell 17, load cell 22, and the pair of bearing load cells 30 and 31, respectively.

The bearing guide plates 28 and 29, in addition to transmitting the load on bolt 27 to bearing load cells 30 and 31, also prevents specimen 12 from buckling when testing in compression. It is important that specimen 12 extends slightly beyond plates 28 and 29 so that grips 18 and 23 can get firm grips on specimen 12 without touching the plates. If the grips touch the plates a portion of the applied bypass load will be transmitted directly to bearing load cells 30 and 31.

In the operation of this invention input signal generator 24 is adjusted to apply a voltage signal to servo control units 14 and 19. This signal if positive will apply compression loads to specimen 12 and if negative will apply tension loads to specimen 12. Voltage controls 25 and 26 are then adjusted to obtain the desired ratio of the applied load to bypass load as indicated by indicators 32 and 33. The ratio of the readings of indicators 34 and 33 is equal to the bearing to bypass ratio. This ratio will remain constant until the specimen fails. The output of input signal generator 24 is increased until the bearing fails. The data are obtained from the readings on indicators 32, 33 and 34. Fatigue bearing-bypass loads can be created by using an input signal generator 24 that generates a cyclic signal.

The advantages of this invention is that it provides a simple approach for bearing-bypass testing that works equally well in tension and compression without a change in apparatus.

What is claimed is:

1. A bearing-bypass testing system for testing a specimen containing a central hole comprising:
   bearing-reaction plate means attached to said specimen by an elongated member extending through said central hole;
   first control means attached to one end of said specimen for applying loads to said specimen either in the direction of or away from said elongated member;
   second control means attached to the other end of said specimen for applying loads to said specimen in the direction opposite to the direction to the load applied by the first control means;
   bearing load cell means fixed relative to said first control means and attached to said bearing-reaction plate means for measuring the resulting loads on said elongated member;
   a signal generator means connected to apply its output signal to said first and second control means to apply either compression or tension loads to said specimen; and
   means for applying fixed ratios of the said output signal to said first and second control means whereby the elongated member loads and bypass loads can be measured.

2. A bearing-bypass testing system according to claim 1 wherein said elongated member is a bolt.

3. A bearing-bypass testing system according to claim 2 wherein said bearing-reaction plate means comprises two bearing-reaction plates bolted to said specimen by said bolt with the specimen between the two bearing-reaction plates.

4. A bearing-bypass testing system according to claim 1 wherein said first and second control means are servo-control means.

5. A bearing-bypass testing system according to claim 1 wherein said bearing load cell means is two bearing load cells located on opposite sides of said specimen equidistance from said elongated member.

6. A bearing-bypass testing system according to claim 1 wherein said means for applying fixed ratios of the said output signal includes means for applying the larger portion of the output signal to said first control means.

7. A bearing-bypass testing method for testing a specimen containing a central hole comprising the steps of:
   fastening bearing-reaction plate means to said specimen by means of an elongated member extending through said central hole;
   applying a first load in either direction to one end of said specimen in line with the center of said elongated member;
   applying a second load, less than said first load, to the other end of said specimen in a direction opposite to which said first load is applied;
   increasing said first and second loads maintaining the same ratio between the two loads; and
   measuring said second loads and the resulting loads transmitted to said bearing-reaction plate means until the specimen fails.

8. A bearing-bypass testing method according to claim 7 wherein said elongated member is a bolt.

9. A bearing-bypass testing method according to claim 8 wherein said bearing-reaction plate means are two plates bolted by said bolt to opposite sides of said specimen.

10. A bearing-bypass testing method according to claim 7 wherein the steps of applying first and second laods comprises the steps of generating an output signal, applying different portions of said output signal to first and second servo control means for simultaneously applying said first and second loads to said specimens.

* * * * *